(12) United States Patent
Herrick et al.

(10) Patent No.: US 8,785,360 B1
(45) Date of Patent: Jul. 22, 2014

(54) METHOD AND SYSTEM FOR COLOR CHANGING CONTACT LENS SOLUTION

(76) Inventors: Ian Herrick, New York, NY (US); Heather Sheardown, Nobleton (CA); Lina Liu, Ancaster (CA); Laura Anne Wells, Toronto (CA); Lyndon William James Jones, Waterloo (CA)

( * ) Notice: Subject to any disclaimer, the term of this patent is extended or adjusted under 35 U.S.C. 154(b) by 67 days.

(21) Appl. No.: 13/209,431

(22) Filed: Aug. 14, 2011

Related U.S. Application Data

(60) Provisional application No. 61/373,808, filed on Aug. 14, 2010.

(51) Int. Cl.
*C11D 3/40* (2006.01)

(52) U.S. Cl.
USPC .......................................................... 510/112

(58) Field of Classification Search
USPC ........................................................... 510/112
See application file for complete search history.

(56) References Cited

U.S. PATENT DOCUMENTS

| | | | |
|---|---|---|---|
| 4,863,627 A * | 9/1989 | Davies et al. | 424/10.32 |
| 2006/0003906 A1 * | 1/2006 | Ohno et al. | 510/112 |

* cited by examiner

*Primary Examiner* — John Hardee

(57) ABSTRACT

A used contact lens is placed in a contact lens receptacle. An aqueous composition is added to the contact lens receptacle, the aqueous composition capable of changing from a first appearance to a second appearance in response to an interaction with the used contact lens after a predetermined period of time.

15 Claims, 5 Drawing Sheets

METHOD AND SYSTEM FOR COLOR CHANGING CONTACT LENS SOLUTION

CLAIM OF PRIORITY

This patent application claims priority to U.S. provisional patent application No. 61/373,808 filed Aug. 14, 2010, which is incorporated by reference herein in its entirety.

TECHNICAL BACKGROUND

Contact lenses have been developed to correct compromised vision when worn. Conventional contact lenses may be comprised of "hard" (rigid gas permeable) material or "soft" (hydrogel) material. "Soft" contact lenses are generally believed to be more comfortable, and are more commonly used than hard contact lenses particularly in recent years.

Even disposable contact lenses (except those designed to be replaced daily) require daily sanitation. Generally, the contact lenses are removed from a user's eyes and placed in a bi-sectioned receptacle (e.g., one lens per section), whereupon a solution is added to remove pollutants, bacteria, and other impurities. Typically, it is recommended that contact lenses be soaked in a solution for at least four hours. However, the recommended usage may not account for actual usage. That is, a contact lens wearer that wears a pair of contact lenses for a long period of time (i.e., a day or more) will naturally accumulate greater amounts of deposits. Also, climate and environmental factors (e.g., areas with greater than normal activity of dust, wind, and/or an ocean elements) may also lead to the accumulation of a greater than normal amount of impurities and deposits such as proteins and lipids, on a daily basis. As a result, sanitizing a pair of contacts may require more time than some contact lens wearers expect. Moreover, diligently keeping track of a daily sanitization process repeated over a considerable period of time (e.g., years) is user intensive—for example, a contacts lens wearer must not only note the time a contact lens is removed from their eye for sanitation, but also accurately calculate a sufficient duration for the lenses to be in the solution for the lenses to be suitable for re-use.

In addition, a contact lens solution is designed to be disposed after every single usage. This is necessary to maintain the efficacy of the solution for lens cleaning and decontamination. However, many users either reuse the same solution (often for several days at a time), and/or merely "top off" their used solution with fresh solution, rather than using fresh solution each time they put their lenses in the case. This reuse and topping off leads to an increased likelihood of eye infection, including very serious and potentially blinding infections, resulting from wearing insufficiently sanitized contact lenses. Reuse and topping off also reduces the likelihood that the lens will be sufficiently cleaned and that all protein and other deposits will be removed during the soaking process, thus making the lens less comfortable to wear and potentially more irritating, which can in turn cause individuals to cease the use of contact lenses entirely. The proteins and other deposits on the contact lenses may also cause infection of the eyes.

Similarly, many eye care specialists recommend that contact lens wearers rinse out their contact lens cases with contact lens solution after each usage (e.g., daily). Here too, contact lens wearers are seldom compliant. Instead of following the recommended instructions, contact lens wearers either do not wash the case out or do so with water, which introduces microbes into the case, which in turn may introduce those same microbes on to the contact lens themselves, and eventually into the contact lens wearer's eye(s).

SUMMARY OF THE APPLICATION

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

A method and system which indicates to the patient that the contact lens solution is spent and therefore should be replaced is described herein. In an embodiment, a used contact lens is placed in a contact lens receptacle. An aqueous composition is added to the contact lens receptacle, the aqueous composition capable of changing from a first appearance to a second appearance in response to an interaction with the used contact lens after a predetermined period of time.

In an embodiment, the aqueous composition includes a protein responsive dye.

In an embodiment, the used contact lens contains protein deposits naturally generated from usage, and the protein responsive dye is reactive to the protein deposits.

In an embodiment, the protein responsive dye comprises at least one of a triphenylmethane dye, a BCA dye (bichinchoninic acid and cupric ion), a Ninhydrin dye, or a bacterial dye.

In an embodiment, the change of the aqueous composition from the first appearance to the second appearance indicates that the deposits have been removed from the contact lens.

In an embodiment, the aqueous composition is discarded after the change from the first appearance to the second appearance. A different used contact lens is added to the contact lens receptacle after removal of the original used contact lens. New aqueous composition is added to the contact lens receptacle to sanitize the different used contact lens.

In an embodiment, the predetermined period of time is less than 24 hours and indicates the amount of time required to disinfect the used contact lens has elapsed.

In an embodiment, the aqueous composition may include an ophthalmic contact lens cleaning solution and a protein responsive dye reactive to a solution on a used contact lens; wherein a reaction between the protein responsive dye and the solution causes the aqueous composition to change from the first appearance to a second appearance when applied to the used contact lens for a predetermined period of time.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternatives, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, and components, have not been described in detail as not to unnecessarily obscure aspects and features of the subject matter.

Portions of the detailed description that follows are presented and discussed in terms of a method. Although steps and sequencing thereof are disclosed in figures herein (e.g., FIGS. 1 and 2) describing the operations of this method, such steps and sequencing are exemplary. Embodiments are well suited to performing various other steps or variations of the steps recited in the flowchart of the figure herein, and in a sequence other than that depicted and described herein.

Figure 1:
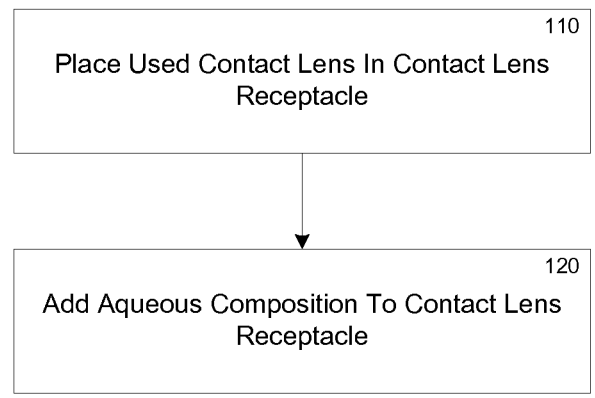
FIG. 1 depicts a flowchart for a process of daily sanitization of used contact lens in accordance with an embodiment of the claimed subject matter.

FIG. 1 depicts a flowchart for a process of sanitization of used contact lens. Flowchart 100 describes a process for a user or contact lens wearer to sanitize used contact lenses. At step 110, a used contact lens is placed in a contact lens receptacle. A worn contact lens may be a contact lens that has been worn by a contact lens wearer and has had significant contact with the contact lens wearer's eye. A contact lens receptacle may be any suitable container for holding contact lenses for sanitation purposes, such as the contact lens receptacle described below with respect to FIG. 3.

At step 120, an aqueous composition is added to the contact lens receptacle. The aqueous composition is capable of changing from a first appearance to a second appearance in response to an interaction with the worn contact lens after a predetermined period of time. For example, the aqueous composition may appear as a first color and change to appearing as a second color after residing in the contact lens receptacle for the predetermined period of time. According to one embodiment, the color change (or change in appearance) is brought about by a reaction between the aqueous composition and components associated with the used contact lens.

The aqueous composition may be a type of contact lens solution that changes appearance to indicate to a contact lens user that the used contact lens has been sufficiently sanitized since a time to sanitize a used contact lens has elapsed; and may also indicate that the user should replace old contact lens solution with fresh contact lens solution. The change in appearance is made possible the presence of a protein responsive dye with color changing properties existing within the aqueous composition, which reacts with certain proteins or lipids that can accumulate on used contact lenses through the course of ordinary usage. Once the used lens is soaked in the aqueous composition, the removal of the accumulated proteins by the lens cleaning solution may trigger a reaction with the protein responsive dye of the aqueous composition, and thus cause the aqueous composition to change from a first appearance to a second appearance. It is understood that protein accumulation takes place while a contact lens is being used or in contact with a wearer's eye and that the reaction takes place when the used lens with the accumulated proteins is placed in contact with the aqueous solution. The protein responsive dye, after reaction with accumulated proteins on a used contact lens, causes a change in the aqueous solution from a first appearance to a second appearance. Thus, in an embodiment, the aqueous composition comprises a generic (multi-purpose) contact lens cleaning solution known in the art, and a protein responsive dye.

It is understood that no change in appearance of the aqueous composition would take place while the aqueous composition is in storage, such as while stored in a contact lens solution bottle. The reaction between the protein responsive dye of the aqueous composition and the protein accumulated on a used contact lens is an automatic one-step reaction and the change in appearance is noticeable as soon as the reaction takes place. It is also understood that while the aqueous composition may change from a first appearance to a second appearance, any change in appearance or color would not permanently stain the used contact lens in any way. Any residual coloring that occurs from the soakage will dissipate from the contact lens in a safe manner after a wearer puts the sanitized contact lens on their eye.

An example of a protein that may accumulate on a used contact lens is lysozyme. Lysozyme is a 14 kDa, positively charged protein (pI~11). Lysozyme accumulation on a contact lens may take place over the course of usage of the contact lens by a contact lens wearer, forming lysozyme deposits. The lysozyme deposits may react with the protein responsive dye of the aqueous composition. The protein responsive dye itself may be a protein assay, and the protein responsive dye may comprise any one of a triphenylmethane protein dye, a 3-(4-carboxybenzoyl)-2-quinoline-carboxaldehyde (QBQCA) protein kit, a (2,2-Dihydroxyindane-1,3-dione) (Ninhydrin) protein responsive dye, or a bacterial dye. A triphenylmethane protein has the chemical formula of $(C_6H_5)_3CH$. All protein responsive dyes and protein assays described above are recognized and known by one skilled in the art.

In an embodiment, the protein responsive dye may also comprise a bicinchoninic acid (BCA) dye. Supposing the protein responsive dye is a BCA dye and further including a cupric ion, a 5% BCA protein responsive dye within an aqueous composition is sufficient to trigger a color change reaction with lysozyme deposits.

While certain surfactants from the contact lens solution may block the protein responsive dye from changing the color or appearance of the aqueous composition, the blockage of the protein responsive dye may be caused by chelation or the presence of chelating agents such as ethylene diamine tetra acetic acid (EDTA), the pH of the aqueous solution being too acidic, or amines existing in the contact lens solution which may prevent the color change reaction from taking place.

In one embodiment, the effects of EDTA are overcome by the addition of a copper sulphate reagent to the aqueous composition.

In some instances, the presence of free amines may lead to premature color changes. As a result, the pH of the contact lens solution may be adjusted to account for the presence of free amines, such that any color change experienced is not premature.

As discussed, the change in appearance of the aqueous composition from a first appearance to a second appearance indicates to a user that sufficient time has elapsed and that the aqueous composition should be replaced. Since the aqueous composition needs to be replaced, the change in appearance may also serve as an indication that the contact lens has been sanitized and also that it is time to discard the aqueous composition in favor of new aqueous composition to sanitize further contact lenses. Typically, the change in appearance will take place during a predetermined time, which may be any amount of time less than 24 hours in order to comply with recommended times for leaving contact lenses in contact lens solution to allow for proper sanitation of the contact lenses.

Figure 2:
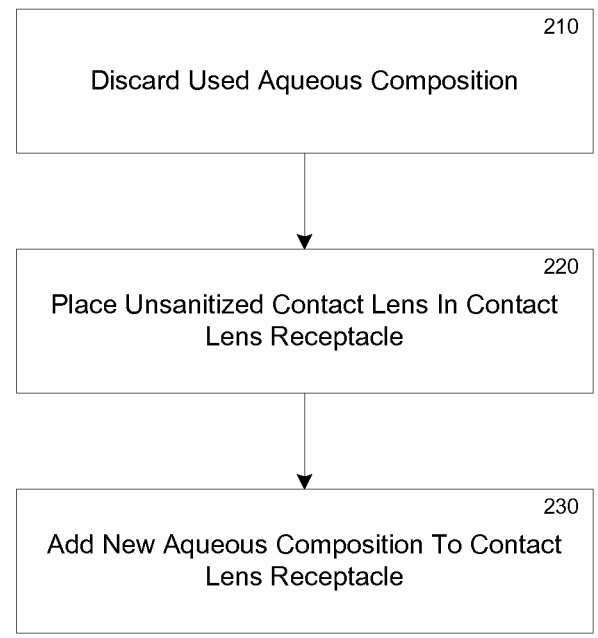
FIG. 2 depicts a flowchart for a process of discarding aqueous composition used during daily sanitization of used contact lens in accordance with an embodiment of the claimed subject matter.

FIG. 2 depicts a flowchart for a process of discarding aqueous composition used during daily sanitization of used contact lens in accordance with an embodiment. The process of discarding aqueous composition is depicted by flowchart 200. At step 210, the used aqueous composition is discarded from the contact lens receptacle. This may occur, for example, after a user has noticed that the aqueous composition has changed from a first appearance to a second appearance.

At step 220, an unsanitized used contact lens is placed in the contact lens receptacle. The unsanitized used contact lens is placed in the contact lens receptacle to start the sanitation process of the unsanitized used contact lenses.

At step 230, fresh aqueous composition is added to the contact lens receptacle to facilitate sanitation of the unsanitized used contact lens.

As discussed above, the aqueous composition changes from a first appearance to a second appearance based on a reaction with protein from a used contact lens in a contact lens receptacle to signal to a user or contact lens wearer that the aqueous composition should be replaced. Since the aqueous composition is being replaced, the color change may also serve as an indication that the contact lenses may be sufficiently sanitized. The change in appearance takes place after a predetermined time, typically greater than 4 hours but less than 16 hours.

The aqueous composition contains a generic contact lens solution, and may contain a protein responsive dye up to a total concentration of 5%. A BCA protein responsive dye may be used, at a 5% to 50% concentration range. The protein responsive dye reacts with a protein removed from a used contact solution, such as lysozyme or lactoferrin, which may be at a concentration of 50 µg/ml or less. In one embodiment, the aqueous solution has a pH of approximately 8, and preferably 7.4.

The aqueous composition may include an ophthalmic contact lens cleaning solution; and a protein reactive dye; wherein a reaction between the protein responsive dye and the protein removed from the lens by the cleaning solution causes the aqueous composition to change from the first appearance to a second appearance when applied to the used contact lens for a predetermined period of time.

The aqueous composition described herein may be used as an indicator to users to change their contact lens solution. The aqueous composition is particularly advantageous to facilitate proper sanitation of contact lenses and ensure that contact lens' wearers will use fresh contact lens solution to clean their used contact lenses. While color has been used as an exemplary characteristic of appearance, various embodiments may include other characteristics of appearance, such as opacity, or pattern. For example, the change in appearance may be localized to some portions of the solution after reaction.

Figure 3A:
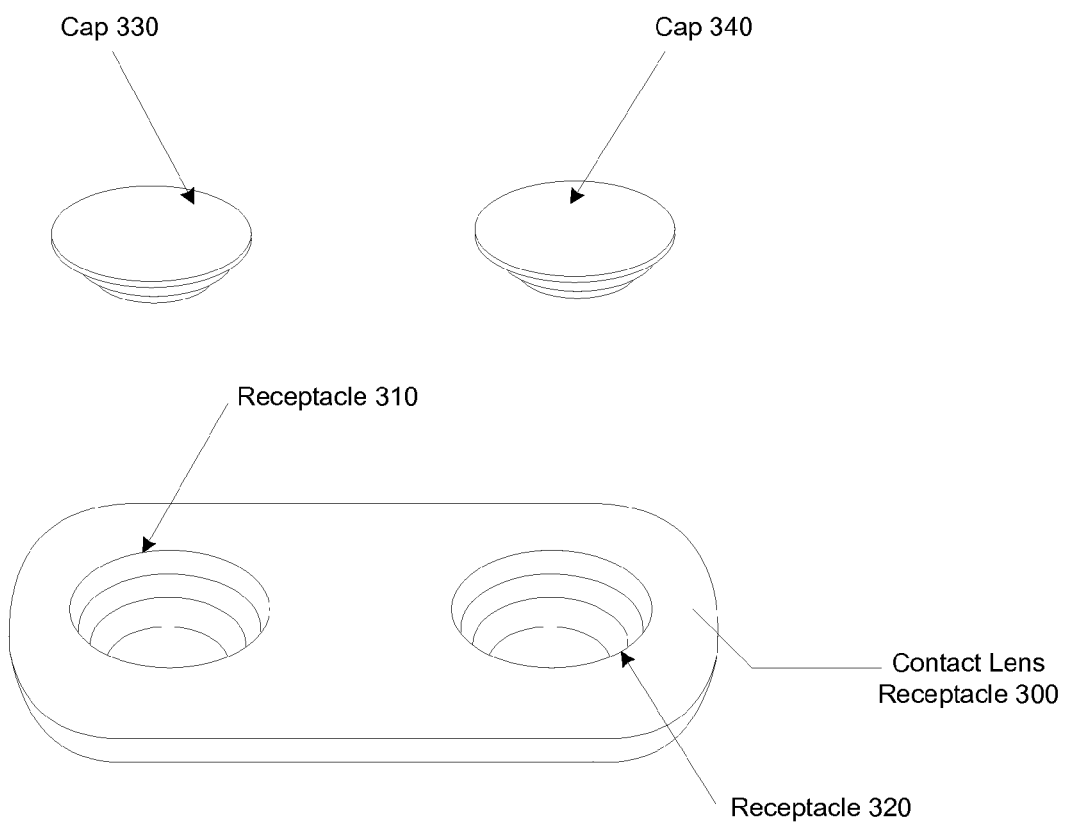
FIG. 3a depicts a diagram of an exemplary system for sanitizing used contact lenses, in accordance with an embodiment of the claimed subject matter.

FIG. 3a depicts an exemplary bi-sectioned contact receptacle 300, in accordance with embodiments of the present claimed subject matter. In one embodiment, the contact lens receptacle may, for example, be a bi-sectioned receptacle made from a hard plastic substance, wherein each section (e.g., section 310, section 320) of the bi-sectioned receptacle is delineated from the other section of the bi-sectioned receptacle, and comprises enough volume to hold a contact lens and a volume of liquid solution. The bi-sectioned receptacle may further contain a cap or lid (e.g., cap 330, 340) operable to enclose the contents of the bi-sectioned receptacle. In some embodiments, each section of the bi-sectioned receptacle has a corresponding cap or lid. Thus, for example, cap 330 corresponds to section 310, and cap 340 corresponds to section 320. In still further embodiments, one or more sections of the bi-sectioned receptacle may be visually represented to be distinguishable from the other. For example, a different graphic icon may be visibly affixed to one or both caps 330, 340.

Figure 3B:
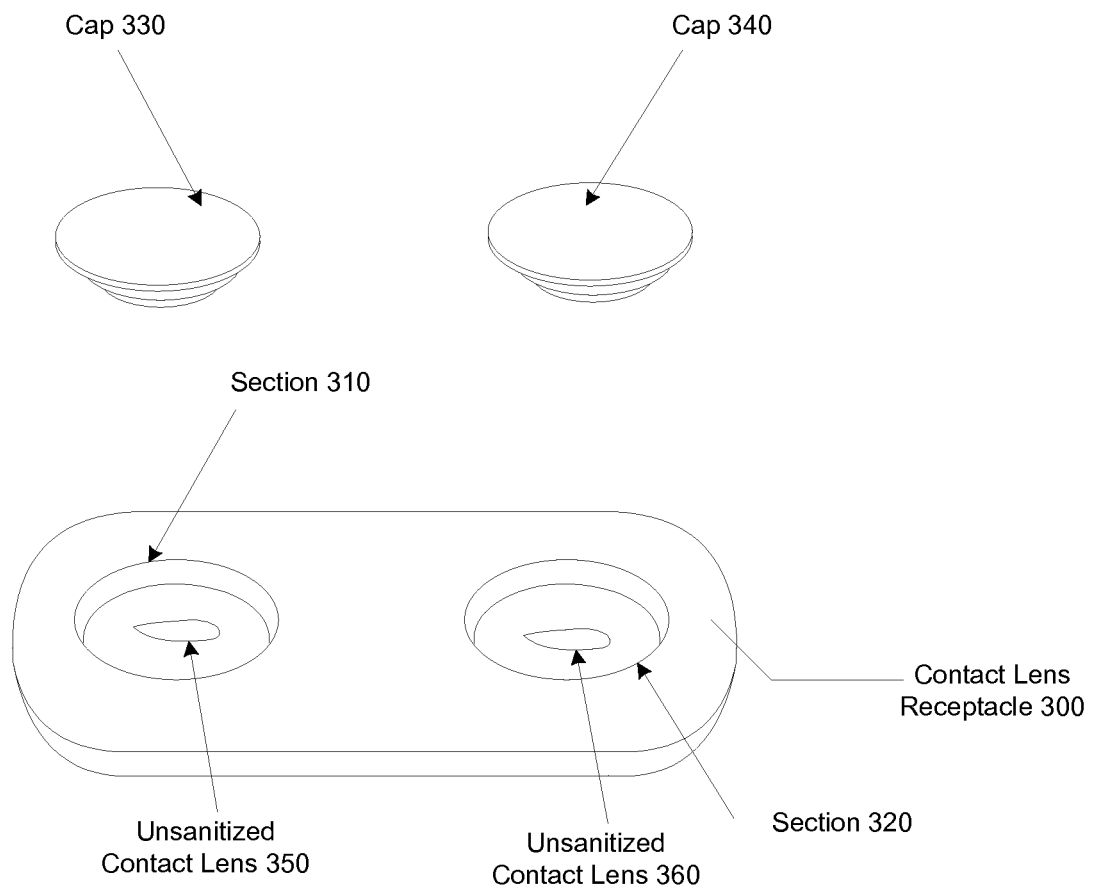
FIG. 3b depicts a diagram of an exemplary receptacle for used lenses containing a used contact lens and an aqueous composition with a first appearance, in accordance with an embodiment of the claimed subject matter.

According to one aspect of the invention, a worn contact lens (e.g., used contact lens 350, 360) may be placed in each section of the bi-sectioned contact receptacle 300, as depicted in FIG. 3b. An aqueous composition, such as the aqueous compositions described above with respect to FIGS. 1 and 2, may then be added to the bi-sectioned contact receptacle 300, such that the used contact lens 350, 360 is sufficient submerged by the aqueous composition. As depicted in FIG. 3b, the aqueous composition has a first appearance (clear).

Figure 3C:
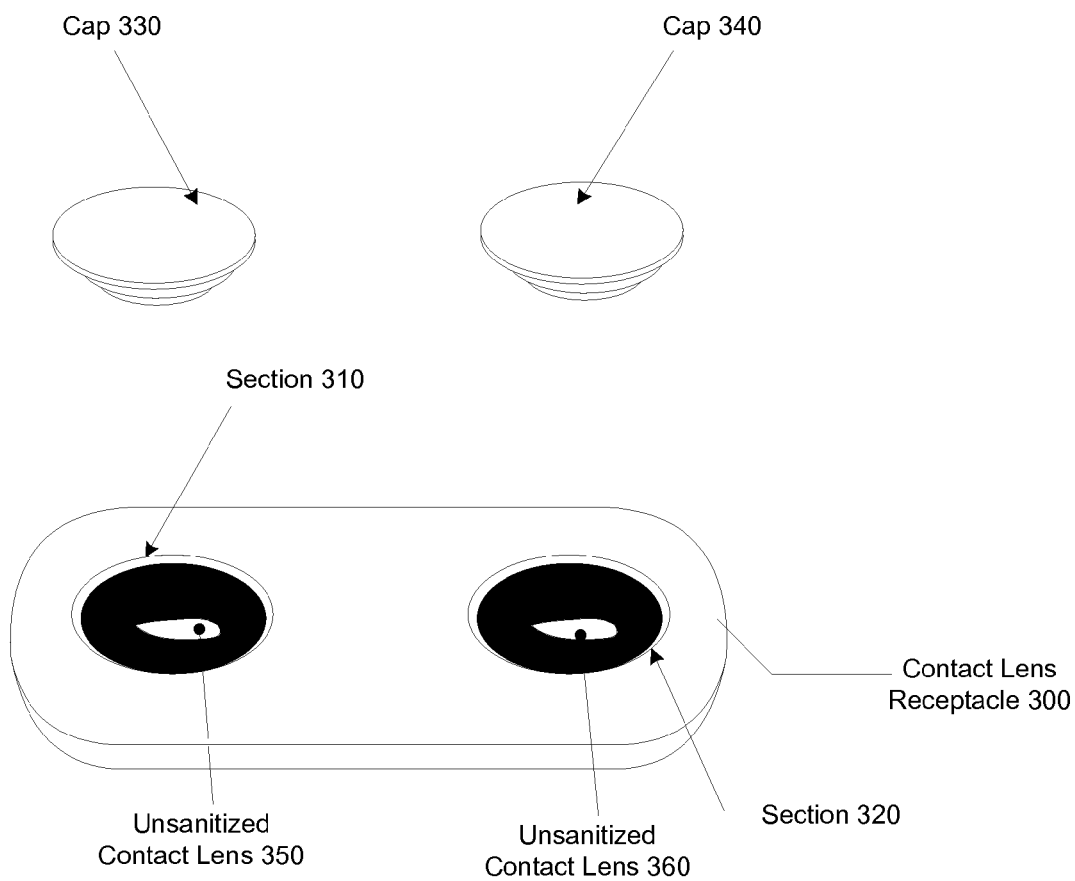
FIG. 3c depicts a diagram of an exemplary receptacle for used contact lenses containing a used contact lens and an aqueous composition with a second appearance, in accordance with an embodiment of the claimed subject matter.

As shown in FIG. 3c, once a used contact lens 350, 360 has been submerged for a predetermined amount of time (typically, for less than 24 hours), the aqueous composition added to the bi-sectioned contact receptacle 300 in FIG. 3b will undergo a change in appearance to a second appearance. As depicted in FIG. 3c, the second appearance is shown as having a significantly darker hue than the first appearance, however, it is to be understood that various embodiments are well suited to changes in the magnitude and/or direction of the change in the appearance. Thus, for example, the first appearance may comprise a lighter and/or clearer appearance, which darkens and/or becomes more opaque from the reaction.

This change in appearance may consist of, but is not limited to, a change in the color of the aqueous composition, a change in the opacity of the aqueous composition, and/or a change in the visual pattern of the aqueous composition. The chance in the appearance may be caused by a reaction between protein deposits on the contact lens (such as naturally occurring protein deposits from normal daily wear) and protein reactive dyes in the aqueous composition. These protein deposits are comprised from proteins naturally formed in and/or around a human eye, such as lysozyme protein deposits, and/or lactoferrin protein deposits. In alternative embodiments, the change in appearance may be caused by a reaction between a protein responsive dye comprised in the aqueous composition and a deposits on a used contact lens, such as those caused by tears from a human eye.

While the contact lens is sanitized by its soaking in the aqueous composition, impurities (including accumulated protein deposits) are removed. A change in the appearance of the aqueous solution indicates that protein deposits have been removed from the contact lens(es).

Although the subject matter has been described in language specific to structural features and/or processological acts, it is to be understood that the subject matter defined in the appended claims is not necessarily limited to the specific features or acts described above. Rather, the specific features and acts described above are disclosed as example forms of implementing the claims.

What is claimed is:
1. A method comprising:
 placing a used contact lens in a contact lens receptacle; and
 adding, from a liquid container, a color changing aqueous composition to the contact lens receptacle, the color changing aqueous composition being capable of changing from a first appearance to a second appearance in response to the color changing aqueous composition's interaction with the used contact lens after a predetermined period of time;

wherein the aqueous composition includes a protein responsive dye comprising at least one of: a BCA dye (bichinchoninic acid and cupric ion), a Ninhydrin dye, and a bacterial dye.

2. The method of claim 1, wherein the used contact lens contains protein deposits from usage, and the protein responsive dye is reactive to the protein deposits.

3. The method of claim 2, wherein the protein deposits comprise lysozyme protein deposits.

4. The method of claim 2, wherein the protein deposits comprise lactoferrin protein deposits.

5. The method of claim 1, wherein the change of the aqueous composition from the first appearance to the second appearance indicates that the protein deposits have been removed from the used contact lens.

6. The method of claim 1, further comprising:
discarding the aqueous composition from the contact lens receptacle;
placing a different used contact lens in the contact lens receptacle; and
adding new aqueous composition to the contact lens receptacle.

7. The method of claim 1, wherein the predetermined period of time is less than 24 hours.

8. The method of claim 1, wherein the predetermined period of time corresponds to an amount of time required to disinfect a used contact lens.

9. A system for sanitizing a contact lens comprising:
a liquid container;
a color changing aqueous composition stored in the liquid container and having a first appearance; and
a contact lens storage receptacle;
wherein the color changing aqueous composition is applied to the used contact lens in the contact lens storage receptacle, and wherein the color changing aqueous composition is configured to change from the first appearance to a second appearance when applied to the used contact lens for a predetermined period of time;

wherein the aqueous composition includes a protein responsive dye comprising at least one of: a BCA dye (bichinchoninic acid and cupric ion), a Ninhydrin dye, and a bacterial dye.

10. The system of claim 9, wherein the used contact lens contains protein deposits from usage, and the protein responsive dye is reactive to the protein deposits.

11. The system of claim 10, wherein the protein deposits comprise at least one of lysozyme protein deposits and lactoferrin protein deposits.

12. The system of claim 9, wherein the predetermined period of time is less than 24 hours.

13. An aqueous composition comprising:
an ophthalmic contact lens cleaning solution;
a protein responsive dye reactive to deposits on a used contact lens;
wherein a reaction between the protein responsive dye and the deposits cause the aqueous composition to change from the first appearance to a second appearance when applied to the used contact lens for a predetermined period of time;
wherein the aqueous composition includes a protein responsive dye comprising at least one of: a BCA dye (bichinchoninic acid and cupric ion), a Ninhydrin dye, and a bacterial dye.

14. The aqueous composition of claim 13, wherein the deposits include protein deposits resulting from usage of the used contact lens, and the protein responsive dye is reactive to the protein deposits.

15. The aqueous composition of claim 13, wherein the protein deposits comprise at least one of: lysozyme protein deposits and lactoferrin protein deposits.

\* \* \* \* \*